US010772944B2

(12) United States Patent
Lubitz et al.

(10) Patent No.: US 10,772,944 B2
(45) Date of Patent: Sep. 15, 2020

(54) BACTERIAL GHOSTS FOR THE TREATMENT OF CANCER

(71) Applicant: BIRD-C GMBH, Vienna (AT)

(72) Inventors: Werner Lubitz, Klosterneuburg/Kritzendorf (AT); Pavol Kudela, Dunajska Luzna (SK); Marek Sramko, Bratislava (SK)

(73) Assignee: BIRD-C GMBH, Vienna (AT)

( * ) Notice: Subject to any disclaimer, the term of this patent is extended or adjusted under 35 U.S.C. 154(b) by 18 days.

(21) Appl. No.: 16/071,958

(22) PCT Filed: Jan. 20, 2017

(86) PCT No.: PCT/EP2017/051218
§ 371 (c)(1),
(2) Date: Jul. 23, 2018

(87) PCT Pub. No.: WO2017/125564
PCT Pub. Date: Jul. 27, 2017

(65) Prior Publication Data
US 2019/0030146 A1    Jan. 31, 2019

Related U.S. Application Data

(60) Provisional application No. 62/281,836, filed on Jan. 22, 2016.

(30) Foreign Application Priority Data

Jan. 22, 2016   (EP) ..................... 16152445

(51) Int. Cl.
| A61K 31/05 | (2006.01) |
| A61K 39/00 | (2006.01) |
| A61K 39/39 | (2006.01) |
| A61K 31/555 | (2006.01) |
| A61K 31/675 | (2006.01) |
| A61K 31/704 | (2006.01) |
| A61K 39/108 | (2006.01) |
| A61K 31/282 | (2006.01) |
| A61K 31/7028 | (2006.01) |
| A61P 35/00 | (2006.01) |
| A61K 31/136 | (2006.01) |
| A61K 31/69 | (2006.01) |

(52) U.S. Cl.
CPC .......... *A61K 39/0011* (2013.01); *A61K 31/05* (2013.01); *A61K 31/282* (2013.01); *A61K 31/555* (2013.01); *A61K 31/675* (2013.01); *A61K 31/704* (2013.01); *A61K 31/7028* (2013.01); *A61K 39/00* (2013.01); *A61K 39/0258* (2013.01); *A61K 39/39* (2013.01); *A61P 35/00* (2018.01); *A61K 31/136* (2013.01); *A61K 31/69* (2013.01); *A61K 2039/545* (2013.01); *A61K 2039/57* (2013.01); *A61K 2039/585* (2013.01); *A61K 2300/00* (2013.01); *Y02A 50/474* (2018.01)

(58) Field of Classification Search
None
See application file for complete search history.

(56) References Cited

U.S. PATENT DOCUMENTS

| 7,361,360 | B2 | 4/2008 | Kitabwalla et al. |
| 7,740,872 | B2 | 6/2010 | Kitabwalla et al. |
| 7,968,323 | B2 | 6/2011 | Lubitz |
| 8,435,531 | B2 | 5/2013 | Kitabwalla et al. |
| 9,790,260 | B2 | 10/2017 | Lubitz |
| 2002/0102602 | A1* | 8/2002 | Yuqiu ............... C07K 14/47 435/7.1 |
| 2003/0003511 | A1 | 1/2003 | Lubitz et al. |
| 2008/0031900 | A1 | 2/2008 | Palucka et al. |
| 2010/0196411 | A1 | 8/2010 | Duke et al. |
| 2011/0172826 | A1 | 7/2011 | Amodei et al. |
| 2012/0040829 | A1 | 2/2012 | Lubitz et al. |
| 2013/0115245 | A1 | 5/2013 | Lubitz |

FOREIGN PATENT DOCUMENTS

| AU | 747328 | 5/2002 |
| AU | 778166 | 11/2004 |
| EP | 0000272 | 1/1979 |
| EP | 1897557 | 3/2008 |
| EP | 2591798 | 5/2013 |
| JP | 2002538198 | 11/2002 |
| JP | 2003521494 | 7/2003 |
| JP | 2009528987 | 8/2009 |
| WO | 9906567 | 2/1999 |
| WO | 2009090093 | 7/1999 |
| WO | 0053163 | 9/2000 |
| WO | 0220042 | 3/2002 |
| WO | 03006630 | 1/2003 |

(Continued)

OTHER PUBLICATIONS

U.S. Appl. No. 13/665,145, Final Office Action dated Jun. 26, 2014, 10 pages.
U.S. Appl. No. 13/665,145, Final Office Action dated Oct. 20, 2015, 11 pages.
U.S. Appl. No. 13/665,145, Non-Final Office Action dated Jun. 1, 2015, 11 pages.
U.S. Appl. No. 13/665,145, Non-Final Office Action dated Oct. 24, 2016, 13 pages.
U.S. Appl. No. 13/665,145, Non-Final Office Action dated Jan. 17, 2014, 7 Pages.
U.S. Appl. No. 13/665,145, Notice of Allowance dated Jun. 16, 2017, 9 pages.

(Continued)

*Primary Examiner* — Padmavathi Baskar
(74) *Attorney, Agent, or Firm* — Kilpatrick Townsend & Stockton LLP

(57) ABSTRACT

The present invention relates to a composition comprising Bacterial Ghosts, optionally an active agent, and a pharmaceutically acceptable carrier and/or excipient for use in the treatment of cancer.

18 Claims, 9 Drawing Sheets

(56) References Cited

FOREIGN PATENT DOCUMENTS

| | | |
|---|---|---|
| WO | 2004058157 | 7/2004 |
| WO | 2010121180 | 10/2010 |
| WO | 2015035606 | 3/2015 |
| WO | 2016000619 | 1/2016 |

OTHER PUBLICATIONS

Agata et al., Expression of the PD-1 Antigen on the Surface of Stimulated Mouse T and B Lymphocytes, International Immunology, vol. 8, No. 5, May 1996, pp. 765-772.
Ardon et al., Adjuvant Dendritic Cell-Based Tumour Vaccination for Children with Malignant Brain Tumours, Pediatr Blood Cancer, vol. 54, Issue 4, Apr. 2010, pp. 519-525.
Bald et al., Immune Cell-Poor Melanomas Benefit From PD-1 Blockade After Targeted Type I IFN Activation, Cancer Discov, vol. 4, No. 6, Jun. 2014, pp. 674-687.
Bennett et al., Program Death-1 Engagement Upon TCR Activation Has Distinct Effects on Costimulation and Cytokine-Driven Proliferation: Attenuation of ICOS, IL-4, and IL-21, But Not CD28, IL-7, and IL-15 Responses, The Journal of Immunology, vol. 170, No. 2, Jan. 15, 2003, pp. 711-718.
Blank et al., Interaction of PD-L1 on Tumor Cells With PD-1 on Tumor-Specific T Cells as a Mechanism of Immune Evasion: Implications for Tumor Immunotherapy, Cancer Immunol Immunother, vol. 54, No. 4, Apr. 2005, pp. 307-314.
Bodey et al., Failure of Cancer Vaccines: The Significant Limitations of this Approach to Immunotherapy, Anticancer Research, vol. 20, Issue 4, Jul. 1, 2000, pp. 2665-2676.
Bour-Jordan et al., Intrinsic and Extrinsic Control of Peripheral T-Cell Tolerance by Costimulatory Molecules of the CD28/B7 Family, Immunological Reviews, vol. 241, No. 1, May 2011, pp. 180-205.
De Gruijl et al., Cancer Vaccine Strategies Get Bigger and Better, Nature Medicine, vol. 5, No. 10, Oct. 1, 1999, pp. 1124-1125.
Dong et al., B7-H1, A Third Member of the B7 Family, Co-Stimulates T-Cell Proliferation and Interleukin-10 Secretion, Nature Med., vol. 5, No. 12, Dec. 1999, pp. 1365-1369.
Eko et al., New Strategies for Combination Vaccines Based on the Extended Recombinant Bacterial Ghost System, Vaccine, vol. 17, No. 13-14, Mar. 26, 1999, pp. 1643-1649.
Eppihimer et al., Expression and Regulation of the PD-L1 Immunoinhibitory Molecule on Microvascular Endothelial Cells, Microcirculation, vol. 9, No. 2, Apr. 2002, pp. 133-145.
Fields et al., Murine Dendritic Cells Pulsed With Whole Cell Tumor Lysates Mediate Potent Antitumor Immune Responses in Vitro and in Vivo, Proc. Natl. Acad. Sci. USA, vol. 95, No. 16, Aug. 4, 1998, pp. 9482-9487.
Flavell et al., The Polarization of Immune Cells in the Tumour Environment by TGFβ, Nat Rev Immunol, vol. 10, Jul. 9, 2010, pp. 554-567.
Forni et al., Immunoprevention of Cancer: Is the Time Ripe, Cancer Research, vol. 60, No. 10, May 2000, pp. 2571-2575.
Freeman et al., Engagement of the Pd-1 Immunoinhibitory Receptor by a Novel B7 Family Member Leads to Negative Regulation of Lymphocyte Activation, J Exp. Med., vol. 192, No. 7, Oct. 2, 2000, pp. 1027-1034.
Gabrilovich et al., Coordinated Regulation of Myeloid Cells by Tumours, Nat Rev Immunol, vol. 12, No. 4, Mar. 22, 2012, pp. 253-268.
Gao et al., Overexpression of PD-L1 Significantly Associates with Tumor Aggressiveness and Postoperative Recurrence in Human Hepatocellular Carcinoma, Clin. Cancer Res., vol. 15, No. 3, Feb. 1, 2009, pp. 971-979.
Ghebeh et al., The B7-H1 (PD-L1) T Lymphocyte-Inhibitory Molecule is Expressed in Breast Cancer Patients with Infiltrating Ductal Carcinoma: Correlation with Important High-Risk Prognostic Factors, Neoplasia, vol. 8, No. 3, Mar. 2006, pp. 190-198.

Hamanishi et al., Programmed Cell Death 1 Ligand 1 and Tumor-Infiltrating CD8+ T Lymphocytes are Prognostic Factors of Human Ovarian Cancer, Proc. Natl. Acad. Sci., vol. 104, No. 9, Feb. 27, 2007, pp. 3360-3365.
Haslberger et al., Activation, Stimulation and Uptake of Bacterial Ghosts in Antigen Presenting Cells, Journal of Biotechnology, vol. 83, Issue 1-2, Sep. 2000, pp. 57-60.
Hino et al., Tumor Cell Expression of Programmed Cell Death-1 Ligand 1 is a Prognostic Factor for Malignant Melanoma, Cancer, vol. 116, Apr. 1, 2010, pp. 1757-1766.
Iwai et al., Involvement of PD-L1 on Tumor Cells in the Escape From Host Immune System and Tumor Immunotherapy by PD-L1 Blockade, PNAS, vol. 99, No. 19, Aug. 1, 2002, pp. 12293-12297.
Japanese Application No. JP2014-5540437, Office Action dated Jan. 25, 2016, 5 pages.
Konishi et al., B7-H1 Expression on Non-Small Cell Lung Cancer Cells and its Relationship With Tumor-Infiltrating Lymphocytes and their PD-1 Expression, Clinical Cancer Research, vol. 10, No. 15, Aug. 1, 2004, pp. 5094-5100.
Krasko et al., Bacterial Ghosts as Adjuvants in Syngeneic Tumour Cell Lysate-Based Anticancer Vaccination in a Murine Lung Carcinoma Model, Oncology Reports, 2016, May 20, 2016, 8 pages.
Kudela et al., Bacterial Ghosts (BGs)-Advanced Antigen and Drug Delivery System, Vaccine, vol. 28, No. 36, Aug. 16, 2010, pp. 5760-5767.
Lindau et al., The Immunosuppressive Tumour Network: Myeloid-derived Suppressor Cells, Regulatory T Cells and Natural Killer T Cells, Immunology, vol. 138, No. 2, Feb. 2013, pp. 105-115.
Lubitz et al., Applications of Bacterial Ghosts in Biomedicine, Pharmaceutical Biotechnology, vol. 655, Aug. 2009, pp. 159-170.
Michalek et al., Oncolysate-Loaded *Escherichia coli* Bacterial Ghosts Enhance the Stimulatory Capacity of Human Dendritic Cells, Cancer Immunology, Immunotherapy, vol. 66, No. 2, Feb. 2017, pp. 149-159.
Nestle et al., Vaccination of Melanoma Patients With Peptide-or Tumor Lysate-Pulsed Dendritic Cells, Nature Medicine, vol. 4, No. 3, Mar. 1, 1998, pp. 328-332.
Nomi et al., Clinical Significance and Therapeutic Potential of the Programmed Death-1 Ligand/Programmed Death-1 Pathway in Human Pancreatic Cancer, Clin. Cancer Res., vol. 13, No. 7, Apr. 1, 2007, pp. 2151-2157.
Ohigashi et al., Clinical Significance of Programmed Death-1 Ligand-1 and Programmed Death-1 Ligand-2 Expression in Human Esophageal Cancer, Clin. Cancer Res., vol. 11, No. 8, Apr. 15, 2005, pp. 2947-2953.
Okazaki et al., PD-1 and PD-1 Ligands: From Discovery to Clinical Application, Int. Immunol., vol. 19, Issue 7, Jul. 1, 2007, pp. 813-824.
Palucka et al., Boosting Vaccinations with Peptide-Pulsed CD34+ Progenitor-Derived Dendritic Cells Can Expand Long-Lived Melanoma Peptide-Specific CD8+ T Cells in Patients with Metastatic Melanoma, Journal of Immunotherapy, vol. 28, No. 2, Mar. 1, 2005, pp. 158-168.
International Application No. PCT/EP2012/072040, International Search Report and Written Opinion, dated Feb. 6, 2013, 15 pages.
Planes et al., HIV-1 Tat Protein Induces PD-L1 (B7-H1) Expression on Dendritic Cells Through Tumor Necrosis Factor Alpha-and Toll-Like Receptor 4-Mediated Mechanisms, Journal of Virology, vol. 88, No. 12, Jun. 2014, pp. 6672-6689.
Remondo et al., Human Dendritic Cell Maturation and Activation by a Heat-Killed Recombinant Yeast (*Saccharomyces cerevisiae*) Vector Encoding Carcinoembryonic Antigen, Vaccine, vol. 27, No. 7, Feb. 11, 2009, pp. 987-994.
Riedmann et al., Bacterial Ghosts as Adjuvant Particles, Vaccines, vol. 6, No. 2, Apr. 2007, pp. 241-253.
Riley, PD-1 Signaling in Primary T Cells, Immunological reviews, vol. 229, No. 1, 2009, pp. 114-125.
Rosenblatt et al., Dendritic Cell Fusion Vaccines for Cancer Immunotherapy, Expert Opin Biol Ther, vol. 5, Issue 5, May 2005, pp. 703-15.
Schreiber et al., Cancer Immunoediting: Integrating Immunity's Roles in Cancer Suppression and Promotion, Science, vol. 331, No. 6024, Mar. 25, 2011, pp. 1565-1570.

(56) References Cited

OTHER PUBLICATIONS

Shi et al., PD-1 and PD-L1 Upregulation Promotes CD8+ T-Cell Apoptosis and Postoperative Recurrence in Hepatocellular Carcinoma Patients, Int. J. Cancer, vol. 128, No. 4, Feb. 15, 2011, pp. 887-896.

Skornick et al., Inhibition of Growth Metastases in Mice by Immunization With Cholesterol Hemisuccinate-Enriched Tumor Cells, Cancer Letters, vol. 25, No. 2, Dec. 1984, pp. 153-161.

Sonnenborn et al., The Non-Pathogenic *Escherichia coli* Strain Nissle 1917—Features of a Versatile Probiotic, Microbial Ecology in Health and Disease, vol. 21, Nos. 3-4, Sep. 2, 2009, pp. 122-158.

Tamura et al., B7-H1 Costimulation Preferentially Enhances CD28-Independent T-Helper Cell Function, Blood, vol. 97, No. 97, Mar. 15, 2001, pp. 1809-1816.

Thompson et al., Costimulatory B7-H1 in Renal Cell Carcinoma Patients: Indicator of Tumor Aggressiveness and Potential Therapeutic Target, Proc. Natl. Acad. Sci., vol. 101, No. 49, Dec. 7, 2004, pp. 17174-17179.

Thompson et al., Pd-1 is Expressed by Tumor-Infiltrating Immune Cells and is Associated With Poor Outcome for Patients With Renal Cell Carcinoma, Clin. Cancer Res., vol. 13, No. 6, Mar. 15, 2007, pp. 1757-1761.

Thurner et al., Vaccination With Mage-3AI Peptide-Pulsed Mature Monocyte-Derived Dendritic Cells Expands Regression of Some Metastases in Advanced Stage IV Melanoma, J Exp Med, vol. 190, No. 11, Dec. 6, 1999, pp. 1669-1678.

Vibharka et al., Activation-induced Expression of Human Programmed death-1 Gene in T-lymphocytes, Exp Cell Res., vol. 232, Apr. 10, 1997, pp. 25-28.

Wu et al., Immunohistochemical Localization of Programmed Death-1 Ligand-1 (PD-L1) in Gastric Carcinoma and Its Clinical Significance, Acta Histochem, vol. 108, Issue 1, May 10, 2006, pp. 19-24.

Yigit et al., Ovarian Cancer Creates a Suppressive Microenvironment to Escape Immune Elimination, Gynecologic Oncology, vol. 117, Issue 2, May 2010, pp. 366-372.

Zhang et al., PD-1/PD-L1 Interactions Inhibit Antitumor Immune Responses in a Murine Acute Myeloid Leukemia Model, Blood, vol. 114, No. 8, Aug. 20, 2009, pp. 1545-1552.

International Application No. PCT/EP2017/051218, International Search Report and Written Opinion dated Mar. 1, 2017.

Langemann et al., "The bacterial ghost platform system:production and applications", Bioengineered Bugs, 2010, 1:5, 326-336.

Szostak, "Bacterial Ghosts: Non-living Candidate Vaccines", Journal of Biotechnology, vol. 44, Jan. 1996, pp. 161-170.

\* cited by examiner

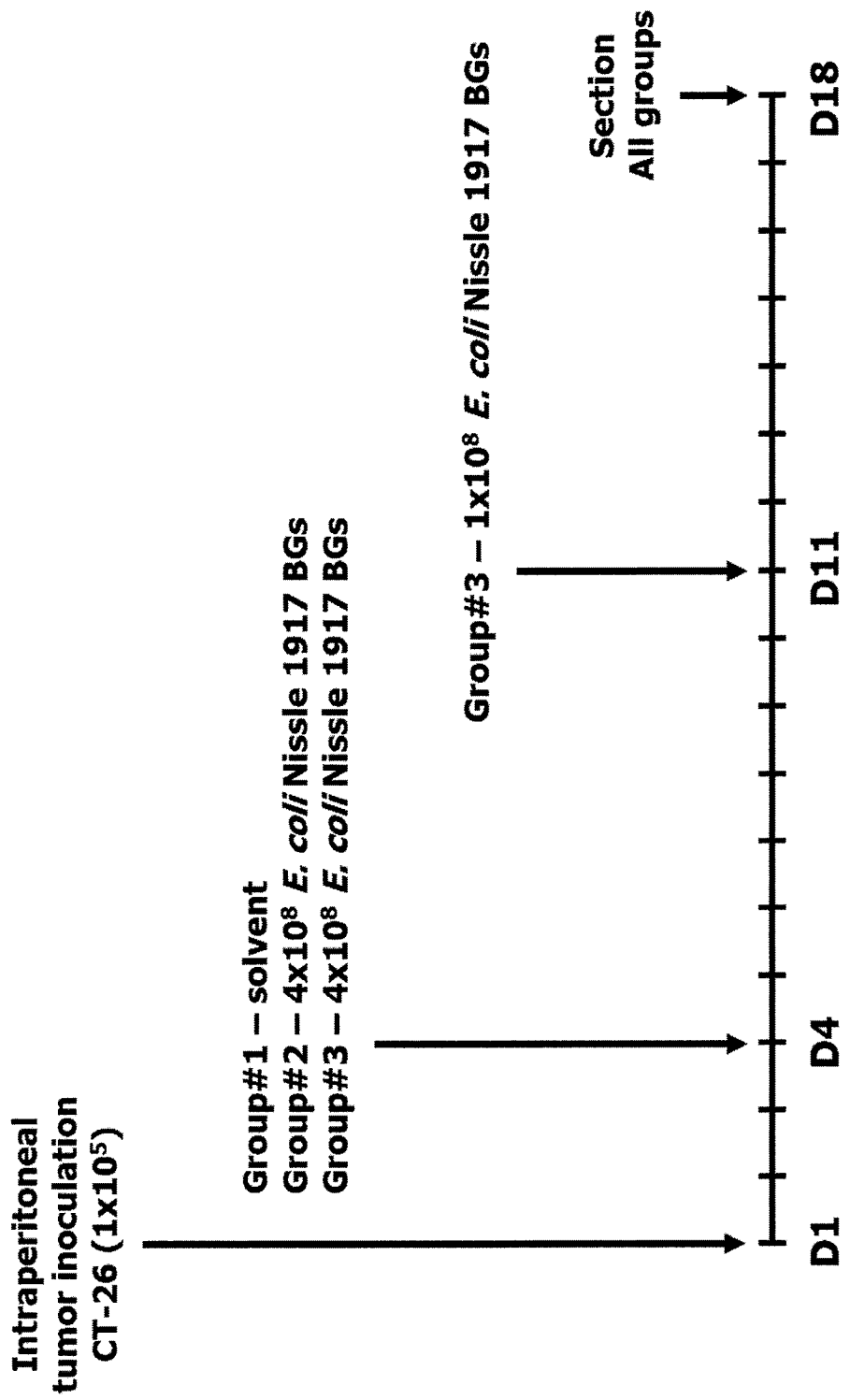
Figure 1. Study scheme and treatment schedule.

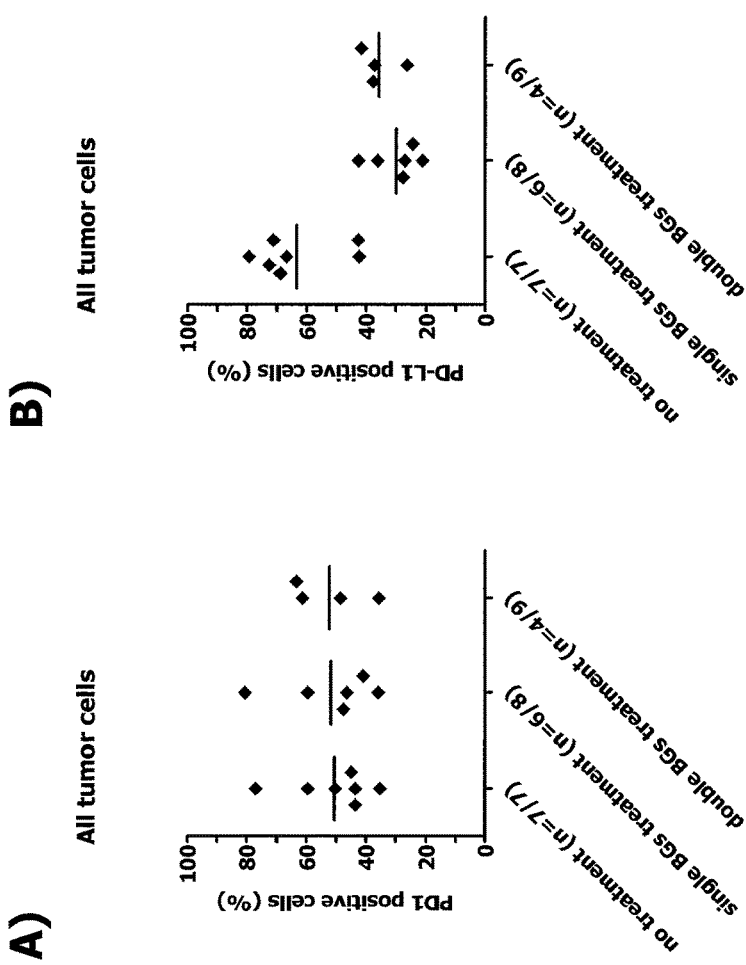
Figure 2. PD1 and PD-L1 expressions by all cells isolated from harvested tumors after treatment of CT26 tumor bearing mice with *E. coli* Nissle 1917 BGs.

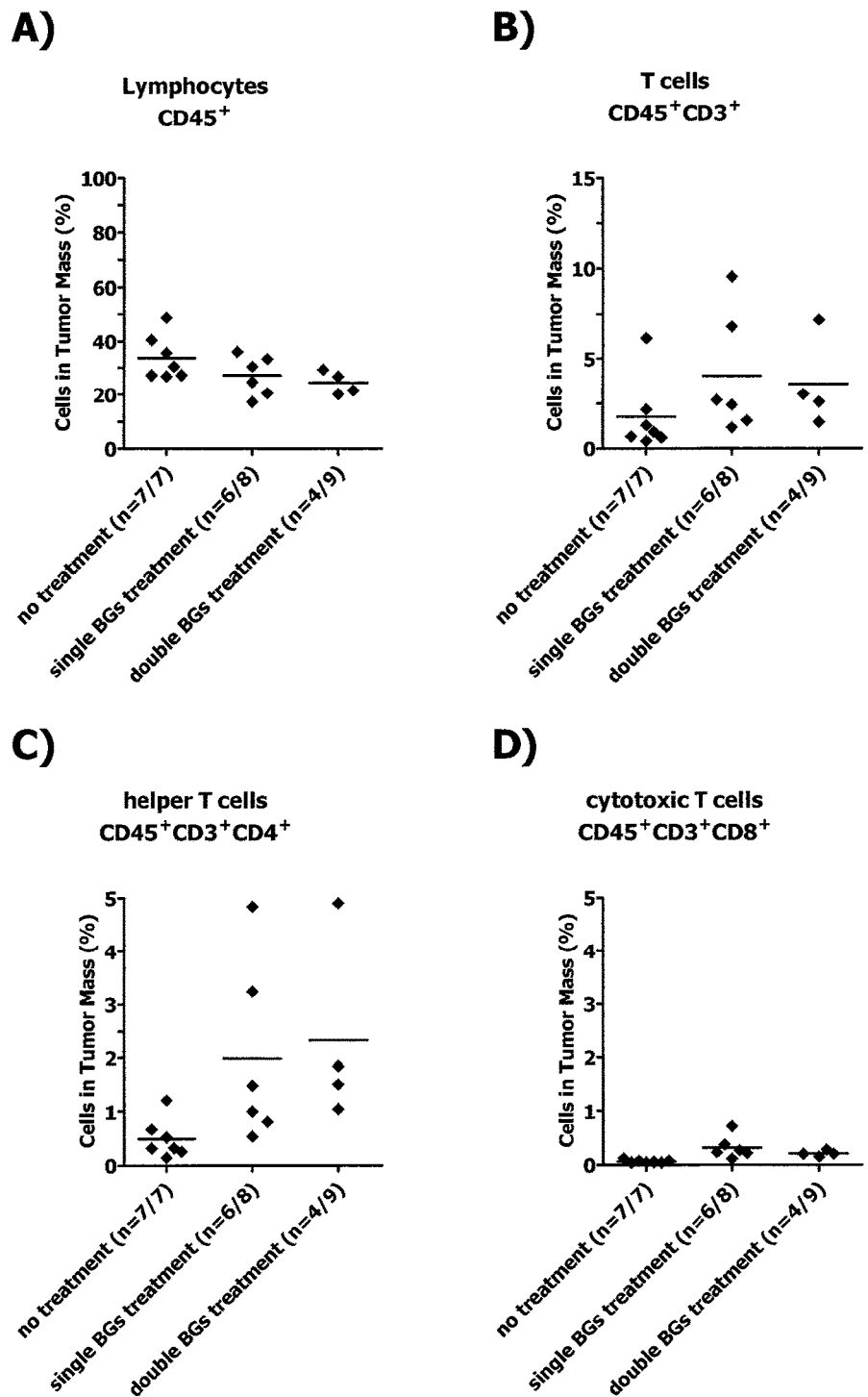
Figure 3. Treatment of CT26 tumor bearing mice with *E. coli* Nissle 1917 BGs modifies the number of lymphocytes present within the tumor microenvironment.

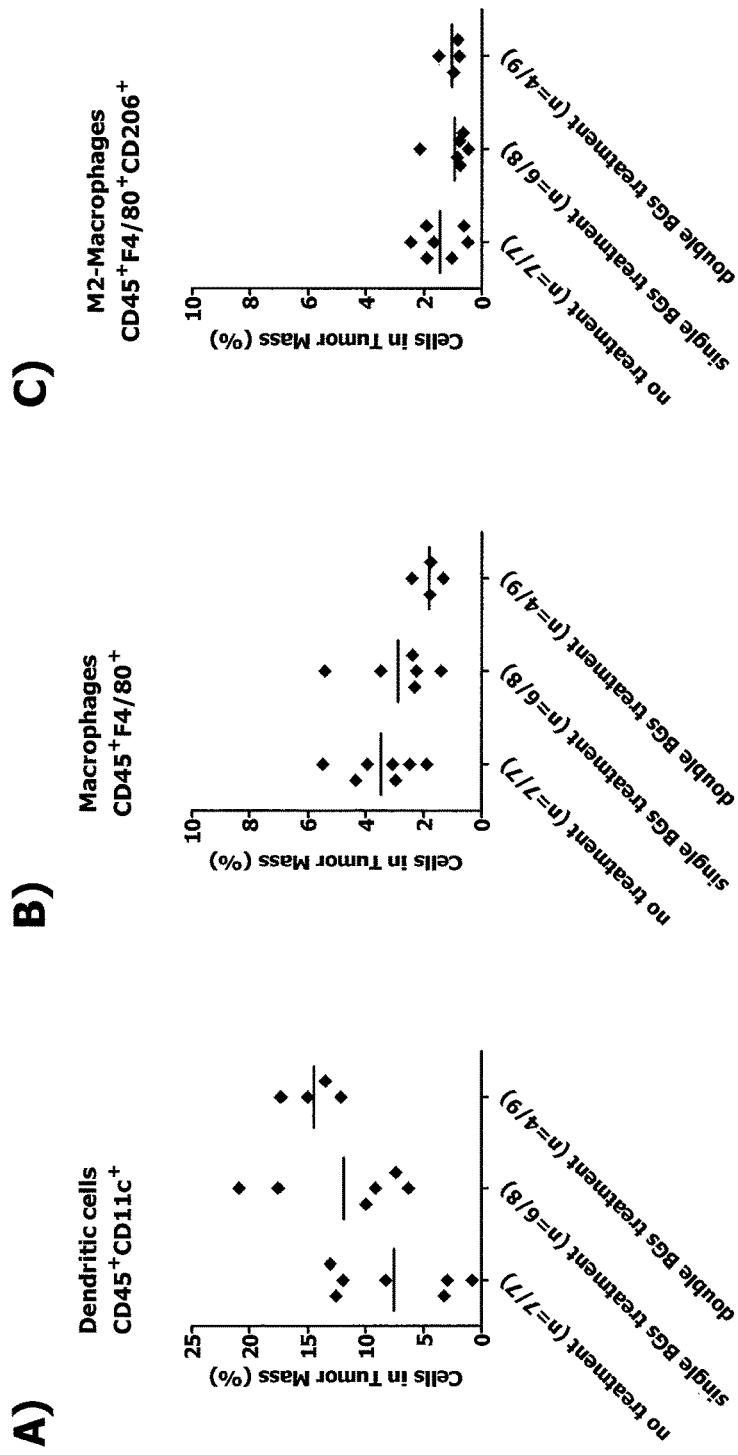
Figure 4. Treatment of CT26 tumor bearing mice with *E. coli* Nissle 1917 BGs alters the number of antigen-presenting cells present within the tumor microenvironment.

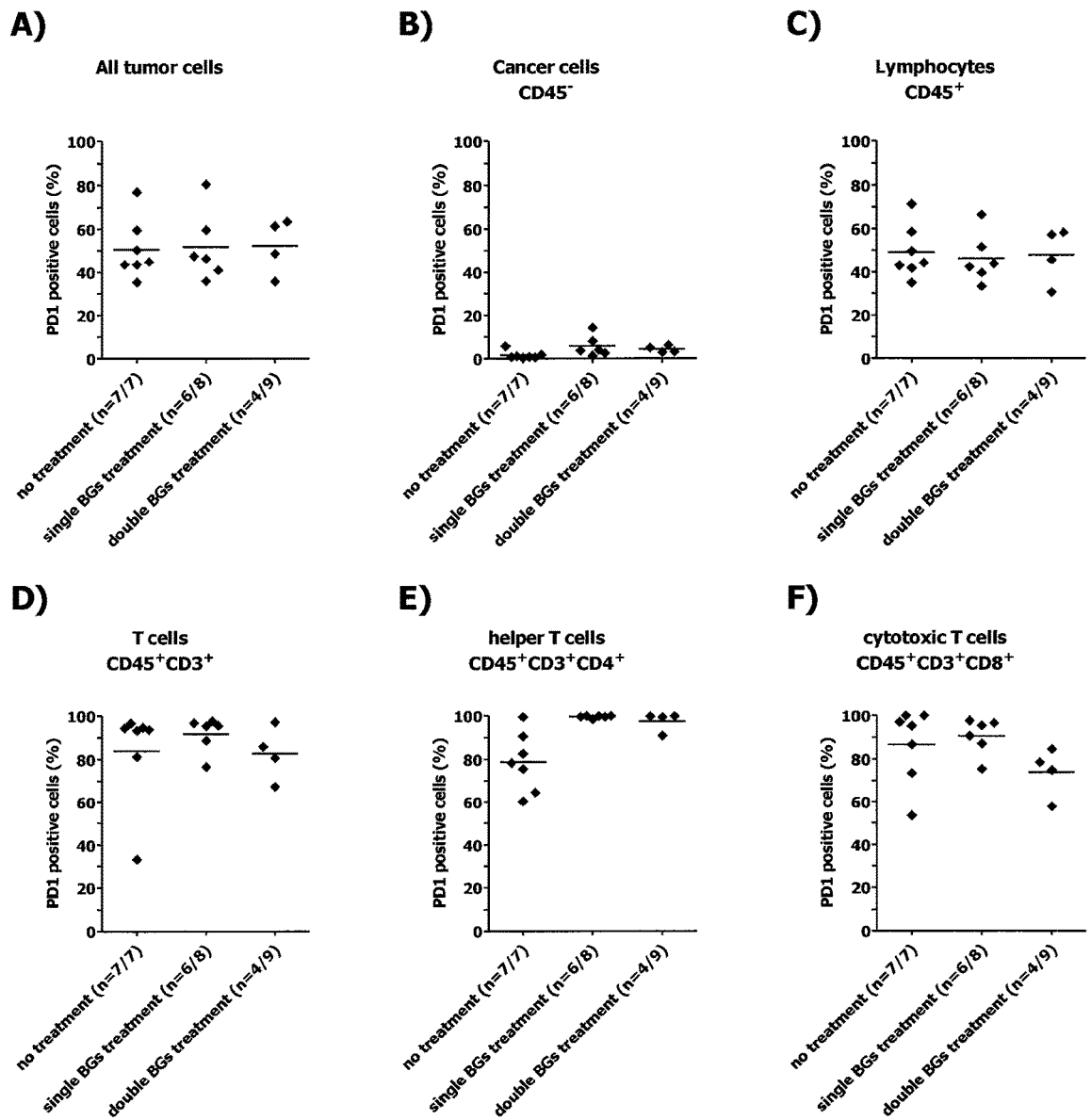
Figure 5. Treatment of CT26 tumor bearing mice with *E. coli* Nissle 1917 BGs doesn't modulate populations of PD1 expressing cancer cells obtained from tumor, but has impact on tumor infiltration by T cells.

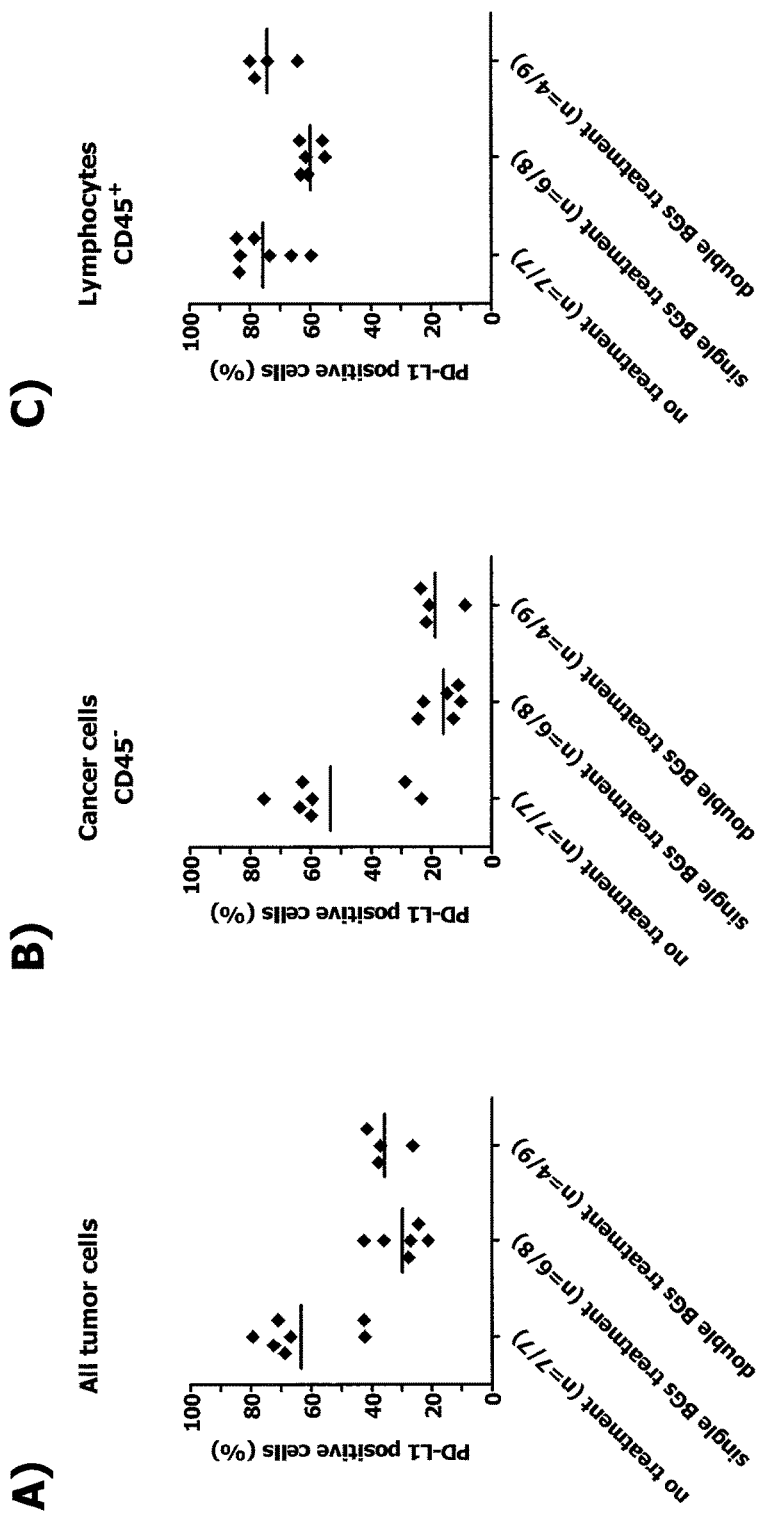
Figure 6. Treatment of CT26 tumor bearing animals with *E. coli* Nissle 1917 BGs reduces the number of PD-L1 positive cells within the tumor microenvironment.

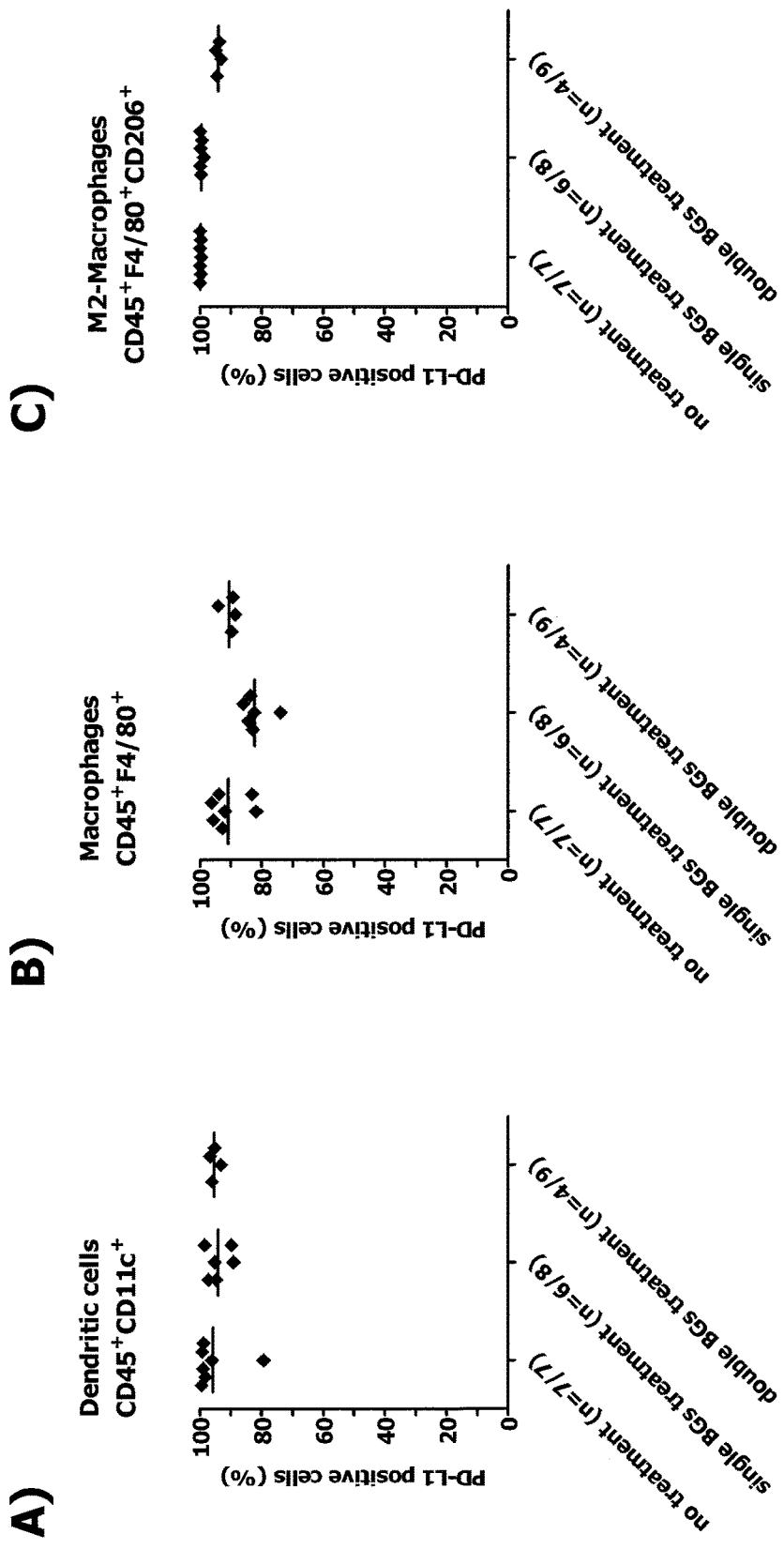
Figure 7. Treatment of CT26 tumor bearing animals with *E. coli* Nissle 1917 BGs modulate populations of PD-L1 positive antigen-presenting cells present within the tumor microenvironment.

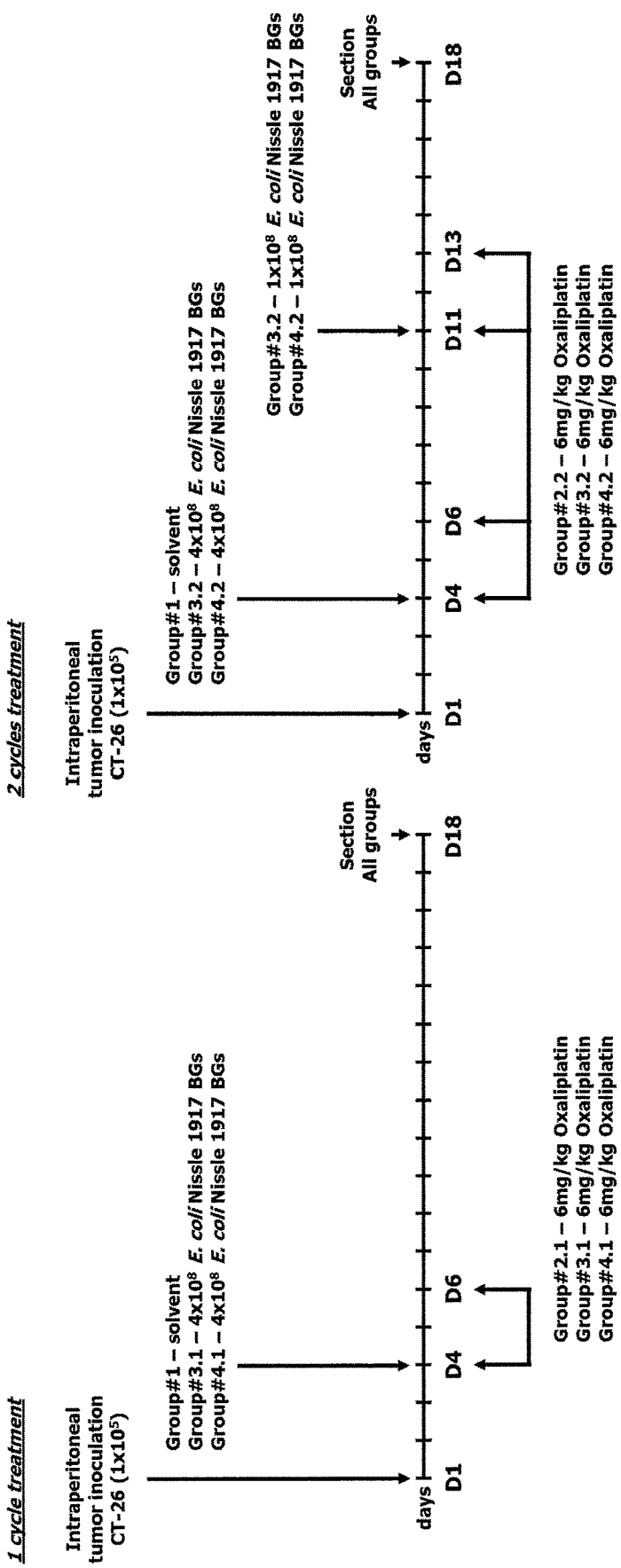
Figure 8. Study scheme and treatment schedule.

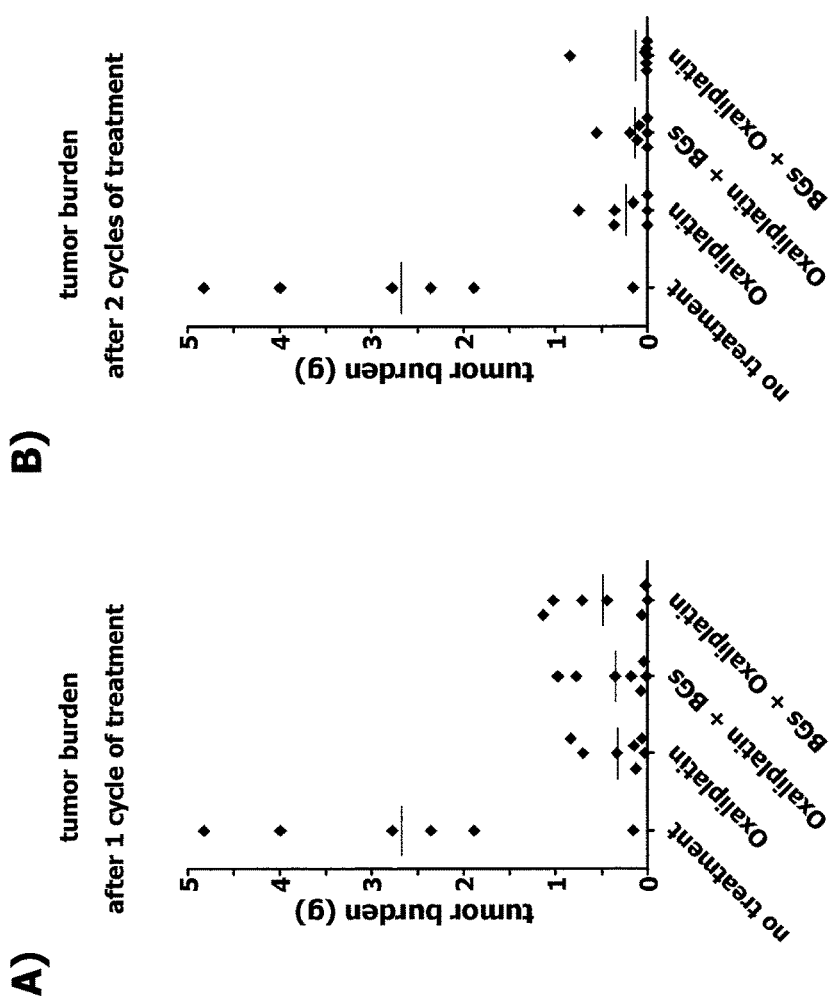
Figure 9. Tumor burden assessment after the treatment of CT26 tumor bearing mice with either Oxaliplatin alone or combined with *E. coli* Nissle 1917 BGs.

BACTERIAL GHOSTS FOR THE TREATMENT OF CANCER

The present invention relates to a composition comprising Bacterial Ghosts (BGs), optionally an active agent, and a pharmaceutically acceptable carrier and/or excipient for use in the treatment of cancer.

Malignant diseases represent a major health problem in all parts of the world and their incidence according to WHO/IARC World Cancer Report 2014 (IARC, 2014) will increase by 57% worldwide in the next 20 years.

Missing symptoms of disease at the early stages of tumor progression are one of the major reasons for diagnosis of cancer only in advanced stages. The complex process of tumor progression is accompanied by rapid cancer cell proliferation, however some of the cancer cells present within the tumor microenvironment (TME) or already disseminated in distant organs can remain on dormancy. Malignancy and proliferation of non-treated tumors usually lead to fatal progression within short time.

Standard treatment strategies for cancer including surgery, chemotherapy and targeted molecular therapy still do not guarantee complete elimination of the disease. In addition, cancer cells exhibit high capability to escape from immunosurveillance. Tumor evasion from immunosurveillance is controlled not only by cancer cells but also via immunosuppression of the patient's own immune cells.

Therefore, it is desirable to revert tumor evasion and to induce strong humoral and cellular immune responses against cancer.

Dendritic cell-based therapy uses tumor cells to stimulate anti-tumor immunity. Therefore dendritic cells are incubated with tumor cells, in particular, with autologous tumor cells or tumor cell lysates, in order to stimulate anti-tumor immunity. The dendritic cells incubated with tumor cells or tumor cell lysates acquire antigens (tumor-specific/-associated) directly from the tumor cells or from the lysates. The dendritic cells bearing the tumor-associated antigens are then used as a vaccine to stimulate the immune system against the tumor. While dendritic cells are necessary to activate a response against cancer cells, they are often ineffective without prior activation because they fail to recognize proliferating cancer cells as dangerous. By activating dendritic cells, using an external stimulus, mature dendritic cells are generated which present the relevant tumor-associated antigens and, thus, induce an effective anti-tumor response.

Such an approach is described, for example, in US 2008/0031900. Therein, antigen-presenting cells such as dendritic cells are activated with GM-CSF and interferon alpha in the presence of one or more cancer cells.

EP 2 591 798 A1 describes a vaccine composition comprising antigen-presenting cells, tumor-associated antigens, and Bacterial Ghosts for use in tumor immunotherapy. Therefore, prior to administration to a patient, antigen-presenting cells were incubated with tumor-associated antigens and Bacterial Ghosts in vitro in order to obtain mature antigen-presenting cells loaded with tumor-associated antigen. The Bacterial Ghosts were found to improve the effectiveness of antigen-presenting cells, in particular dendritic cells, as a tumor vaccine when used in combination with tumor-associated antigens. In particular, an interaction between antigen-presenting cells, Bacterial Ghosts and tumor-associated antigens resulted in stimulation, activation and maturation of the antigen-presenting cells. By administration of such a vaccine composition an immune response against cancer cells is evoked.

A therapeutic approach based on in vitro stimulated antigen-presenting cells such as dendritic cells with or without the use of Bacterial Ghosts requires prior isolation of antigen-presenting cells and the provision of tumor-associated antigens and optionally further the preparation of Bacterial Ghosts.

In a different approach to (re)stimulate the immune system antibodies against Programmed Death-1 (PD1) receptor and its ligand PD-L1 are used.

Interaction of PD1 receptor and its ligand PD-L1 induces intracellular signal transduction that inhibits CD3- and CD28-mediated T cell activation (Riley, 2009 Immunol Rev 229:114-125), which subsequently diminishes T cell activities such as reduction of cell proliferation, IL-2 and IFN-γ secretion as well as other growth factor and cytokine secretion.

Expression of PD1 is frequently found in immune cells such as T cells, B cells, monocytes and natural killer cells, while it is rarely expressed in other human tissues such as muscle, epithelium and neuronal tissues. Furthermore, a high level of PD1 expression is often associated with activation of immune cells. For example, expression of PD1 was up-regulated (visibly in Western Blot) in human T-cell line Jurkat after activation by phytohaemagglutinin (PHA) or phorbol ester (12-0-tetradecanoylphorbol-13-acetate, or TPA) (Vibharka et al., 1997 Exp Cell Res 232:25-28). A similar observation was made in stimulated murine T and B lymphocytes and in primary human CD4$^+$ T cells upon stimulation with anti-CD3 antibody (Agata et al., 1996 Int Immunol 8:765-772; Bennett et al., 2003 J Immunol 170: 711-118). An increase of PD1 expression following stimulation of T effector cells redirects the activated T-effector cells towards exhaustion and reduced immune activities. Therefore, PD1 mediated inhibitory signal plays an important role in immune tolerance (Bour-Jordan et al., 2011 Immunol Rev 241:180-205).

PD-L1 was found constitutively expressed in human heart, lung, thymus and vascular endothelial cells, while ist was expressed at a low level in several other human tissues and cell types including antigen-presenting cells, peripheral blood monocytes and other immune cells (Freeman et al., 2000 J Exp Med 192:1027; Eppihimer et al., 2002 Microcirculation 9:133). Upon stimulation with IFN-γ, IL-12 and type I interferons many of those cell types were found to increase expression levels of PD-L1 (Bald et al., 2014 Cancer Discov 4:674-687; Planes et al., 2014 J Virol 88:6672-6689).

Increased expression of PD1 receptor in tumor-infiltrating lymphocytes and increased expression of PD1 ligand (PD-L1) in tumor cells were reported in varieties of cancers involved in different types of tissues and organs such as lung (Konishi et al., 2004 Clin Cancer Res 10:5094-5100), liver (Shi et al., 2008 Int J Cancer 128:887-896; Gao et al., 2009 Clin Cancer Res 15:971-979), stomach (Wu et al., 2006 Acta Histochem 108: 19-24), kidney (Thompson et al., 2004 Proc Natl Acad Sci 101:17174-17179; Thompson et al., 2007 Clin Cancer Res 13:1757-1761), breast (Ghebeh et al., 2006 Neoplasia 8:190-198), ovary (Hamanishi et al. 2007 Proc Natl Acad Sci 104:3360-3365), pancreas (Nomi et al., 2007 Clin Cancer Res 13:2151-2157), melanocytes (Nino et al., 2010 Cancer 116:1757-1766) and esophagus (Ohigashi et al., 2005 Clin Cancer Res 11:2947-2953). An increased expression of PD1 and PD-L1 in those above mentioned cancers is associated with poor prognosis for survival. In transgenic mice with PD1 gene knockout xenograft cancer cell growth was inhibited which further elucidated the significance of PD1 signaling in the modulation of the immune system for cancer elimination or tolerance (Zhang et al., 2009 Blood 114:1545-1552).

Blocking PD-L1 binding to PD1 receptor by B7-H1Ig or anti-PD-L1 antibody stimulated T cell proliferation and functional activities (Dong et al., 1999 Nature Med 5:1365; Freeman et al., 2000 J Exp Med 192:1027; Tamura et al., 2001 Blood 97:1809; Iwai et al., 2002 PNAS 99:12293), enhanced immune responses against tumor growth and viral infection (Iwai et al., 2002 PNAS 99:12293) suggesting that inhibition of PD-L1/PD1 signaling may activate immune responses against cancer cell growth and also against viral infection and virus propagation in human. Therapeutic modulation of PD-L1- and PD1-mediated signaling using antagonistic molecules may revert immune cells from tolerance and restimulate them to eliminate cancer and chronic viral infection (Blank et al., 2005 Cancer Immunol Immunother 54:307; Okazaki et al., 2007 Int Immunol 19:813).

In order to stimulate anti-tumor immunity WO 2015/035606 A1 provides antibodies that specifically bind to Programmed Death-1 (PD1) receptor and inhibit PD1-mediated cellular signaling and activities in immune cells in order to treat or diagnose cancer, infectious diseases or other pathological disorders modulated by PD1-mediated functions.

Similarly, WO 2016/000619 A1 provides antibodies that specifically bind to Programmed Death-1 ligand (PD-L1) and inhibit PD-L1-mediated cellular signaling and activities in immune cells in order to treat or diagnose cancer, infectious diseases or other pathological disorders modulated by PD-L1-mediated functions.

Antibodies against PD1 and PD-L1 are commercially available but are very expensive which increases the costs of a corresponding cancer treatment.

In summary, the therapeutic approaches to elicit an immune response against cancer pursued up to date mostly require much effort, are time consuming and involve high costs.

Therefore, it is required to provide further therapeutic approaches to efficiently stimulate anti-tumor immunity which at the same time are cost-effective and require less effort.

Therefore, an objective of the invention was to (re)stimulate the patient's immune system to revert the tumor evasion and to build up strong humoral and cellular immune responses against cancer and in particular against patient-specific tumor antigens. It was a further object of the invention to achieve an extended period of stable disease and/or to reduce or eliminate tumor burden. It was a particular object of the invention to achieve cancer remission.

Therefore, the invention provides Bacterial Ghosts and/or a composition comprising Bacterial Ghosts for use in the treatment or prevention of cancer, in particular for use in the treatment of cancer, more particularly for use in the inhibition of tumor progression and/or metastasis.

In particular, the present invention provides a composition comprising Bacterial Ghosts, optionally an active agent, and a pharmaceutically acceptable carrier and/or excipient for use in the treatment and/or prevention of cancer.

The composition comprising Bacterial Ghosts, optionally an active agent and a pharmaceutically acceptable carrier and/or excipient is obtainable without much effort and very cost-effective at the same time.

In a first embodiment the inventive composition for use in the treatment or prevention of cancer does not comprise an active agent. Thus, the composition comprises and in particular consists of (i) Bacterial Ghosts, and (ii) a pharmaceutically acceptable carrier and/or excipient.

Tumors represent complex heterogenous systems built up by cancer cells and distinct non-malignant cell populations including immune cells, cancer-associated fibroblasts, angiogenic vascular cells, and lymphatic endothelial cells actively participating on disease progression all together forming the so called tumor microenvironment (TME) (Lindau, D., Gielen, P., Kroesen, M., Wesseling, P. & Adema, G. J. The immunosuppressive tumour network: myeloidderived suppressor cells, regulatory T cells and natural killer T cells. Immunology 138, 105-15 (2013)).

Moreover, in most cases advanced cancer is accompanied by a complex tumor mass containing cancer cells supplemented with stromal cells, both thymus- and myeloid-derived suppressor cells, and immunosuppressive factors including e.g. IL-10, TGF-β, VEGF, COX, PGE2 and CCL22 inhibiting function and differentiation of dendritic cells (DCs), macrophages, neutrophils and tumor antigen-specific effector T cells (Flavell, R. A., Sanjabi, S., Wrzesinski, S. H. & Licona-Limon, P. The polarization of immune cells in the tumour environment by TGFbeta. Nat Rev Immunol 10, 554-67 (2010); Gabrilovich, D. I., Ostrand-Rosenberg, S. & Bronte, V. Coordinated regulation of myeloid cells by tumours. Nat Rev Immunol 12, 253-68 (2012); Yigit, R., Massuger, L. F., Figdor, C. G. & Torensma, R. Ovarian cancer creates a suppressive microenvironment to escape immune elimination. Gynecol Oncol 117, 366-72 (2010)). Recent reports confirmed that altered functions of immune cells within the TME, e.g. myeloid-derived suppressor cells (MDSCs), tumor-associated macrophages (TAMs), DCs, and regulatory and effector T cells play major roles in tumor evasion from immunosurveillance (Gabrilovich, D. I., Ostrand-Rosenberg, S. & Bronte, V. Coordinated regulation of myeloid cells by tumours. Nat Rev Immunol 12, 253-68 (2012)).

Often in cancer an immunosuppressive tumor microenvironment to escape immune elimination is observed.

Protective T cell immune response can be restored by modulation of the TME leading to elimination of disseminated tumor lesions (Schreiber, R. D., Old, L. J. & Smyth, M. J. Cancer immunoediting: integrating immunity's roles in cancer suppression and promotion. Science 331, 1565-70 (2011).

It has now been found that Bacterial Ghosts are capable of modulating the tumor microenvironment.

In the tumor microenvironment Bacterial Ghosts are able to target dendritic cells (DCs), macrophages, cancer cells, myeloid-derived suppressor cells (MDSC), vascular endothelial cells, T cells, cancer-associated fibroblasts (CAF) due to specific ligand-receptor interaction of bacterial ghost surface components and receptors on the surface of the latter cells.

BGs show no cytotoxic and genotoxic impacts on the viability and metabolic activity of a wide range of tested cells including macrophages, dendritic cells, tumor cells, endothelial cells and epithelial cells. BGs with their intact surface structures are efficiently recognized and phagocytosed by professional APCs, e.g. dendritic cells and macrophages through various surface receptors, e.g. complement receptors and Toll-like receptors. Moreover, further studies using DCs as model of the most professional antigen-presenting cells (professional APCs) revealed that their phagocytic activity and uptake of BGs depend on the bacterial strain used for the production of BGs.

Herein it is shown that Bacterial Ghosts significantly reduce (~50%) the number of PD-L1-positive cells in the TME (FIG. 2B and FIG. 6A). The total number of PD-L1-positive cells in the TME is in particular reduced by at least 10%, preferably by at least 30%, and more preferably by at least 50%. In particular, the reduction of PD-L1-positive cells is due to a reduction of PD-L1 on cancer cells (FIG. 6B) but not on DCs (FIG. 7A). The number of PD-L1-positive cancer cells is preferably reduced by at least 50%, more preferably at least 60% and preferably up to 90%, more preferably up to 80%. PD-L1 is also reduced on TME macrophage population to an extent of 10-20% (FIGS. 7 B and 7C).

Bacterial Ghost application to the TME, in particular intraperitoneal bacterial ghost application to the TME does not change the number of PD1-positive cells in total (FIG. 5A) and not the number of PD1-positive total lymphocytes either (FIG. 5C).

However, Bacterial Ghost application to the TME increased the total number of CD4$^+$ helper T cells ~5-fold (FIG. 3C), in particular at least 2-fold, preferably at least 3-fold and up to 10-fold, preferably up to 7-fold. The PD1-positive fraction of CD4$^+$ helper T cells is increased from 80 to 100% (FIG. 5E). In contrast thereto, Bacterial Ghost application to the TME reduced PD1 receptor on CD8$^+$ cytotoxic T cells (FIG. 5F), in particular to an extent from 10-30%.

An almost 2-fold increase, in particular a 1.5- to 2-fold increase, of the total number of DCs in the TME (FIG. 4A) is observed. This effect is dependent on BG treatment cycles, in particular on the number of BG applications. As a BG cycle dependent decrease of CD45$^+$ lymphocytes (FIG. 3A) is seen, it is speculated, without wishing to be bound by theory, that the observed increase in DCs is either due to a polarization of myeloid cells already present in the TME or to a new infiltration of DCs as consequence of modulation of the cytokine milieu of the TME mediated by BGs.

Application of BGs to the TME reduces the number of M2 macrophages approximately by half (FIG. 4C), in particular by 40-60%. The total number of macrophages is also reduced to the same extent (FIG. 4B). Without wishing to be bound by theory, this can be interpreted by macrophage decrease after uptake of BGs due to apoptosis. As apoptotic macrophages are normally taken up by antigen-presenting cells APCs including DCs this can also explain the DC recruitment seen in FIG. 4A. In this regard it is also remarkable to see an 2-3 fold increase in cytotoxic T cells in TME (FIG. 3).

More general, as a consequence of BG application(s) to the TME a heavily decrease of PD-L1 on cancer cells is observed combined with an increased number of cytotoxic T cells and DCs. The observed BG cycle dependent increase of tumor free mice, two out of eight and four out of nine, after single or double application of BGs, respectively, suggests a direct effect of BGs on the TME and/or enhanced regression of tumor burden due to adaptive immune response.

The inventors have found that the two effects of Bacterial Ghosts, short-time direct effect on the TME and long-time effect by induction of tumor specific immunity, can be used in combination for tumor therapy.

Application of BGs alone and/or BGs carrying defined tumor associated antigens (TAAs) in people predisposed for cancer to an area of potential tumor growth (breast, ovary, colon, other) can be used preventively.

According to the invention, it has been found that administration of Bacterial Ghosts to tumor-bearing mice resulted in increased numbers of PD1-positive CD45$^+$CD3$^+$CD4$^+$ expressing helper T cells, while reduced numbers of PD1-positive CD45$^+$CD3$^+$CD8$^+$ expressing cytotoxic T cells were detected.

Only moderate effect of Bacterial Ghosts on PD1 expression by cancer cells was observed. In contrast thereto, treatment of tumor-bearing animals with Bacterial Ghosts markedly reduced the percentage of cancer cells expressing PD-L1 within the tumor microenvironment.

Besides, increased numbers of tumor-infiltrating CD45$^+$CD3$^+$CD4$^+$ helper T cells and CD45$^+$CD11c$^+$ dendritic cells were observed. In addition, also a very little enhanced number of tumor-infiltrating CD45$^+$CD3$^+$CD8$^+$ cytotoxic T cells was found, while reduced numbers of tumor infiltrating M2 CD45$^+$F4/80$^+$CD206$^+$ macrophages and more significantly of CD45$^+$F4/80$^+$ macrophages were observed.

Most importantly, however, tumor remission was observed in two out of eight animals after single treatment with Bacterial Ghosts and in four out of nine animals after receiving two doses of Bacterial Ghosts.

Therefore, a first embodiment of the present invention is a composition comprising and in particular consisting of (i) Bacterial Ghosts and (ii) a pharmaceutically acceptable carrier and/or excipient for use in the treatment of cancer.

Since application of BGs alone has been shown to be effective, in a preferred embodiment the inventive composition does not comprise an active agent and/or antigen-presenting cells, in particular DCs.

In a second embodiment the inventive composition for use in the treatment or prevention of cancer comprises an active agent. Thus, the composition comprises and in particular consists of (i) Bacterial Ghosts, (ii) an active agent, and (iii) a pharmaceutically acceptable carrier and/or excipient.

According to the invention it has further been found that administration of a combination of Bacterial Ghosts and an active agent, in particular a chemotherapeutic drug such as oxaliplatin results in a reduction of the tumor burden. BGs and active agent can be administered together or separately. Preferably, BGs are administered prior to an active agent.

In the case of repeated administration of Bacterial Ghosts and chemotherapeutic agent, administration of Bacterial Ghosts first resulted in an even greater reduction of the tumor burden than a corresponding treatment wherein the active agent, in particular the chemotherapeutic drug was administered first.

When Bacterial Ghosts loaded with an active agent, in particular a chemotherapeutic active agent, are administered, the Bacterial Ghosts are bound and internalized by cancer cells followed by degradation of the Bacterial Ghosts within the cancer cells. Thereupon, the active agent is released into the cytoplasm of the cancer cells, thereby inducing cell death, in particular immunogenic cell death of the cancer cells. Subsequently, damage-associated molecular patterns and endogenous tumor antigens such as proteins, nucleic acids and degradation products are released from the dying cancer cells. The released tumor-associated antigens are internalized by immature antigen-presenting cells, in particular by immature dendritic cells. Upon maturation of the antigen-presenting cells, in particular of the dendritic cells, the internalized tumor-associated antigens are processed and presented by the mature antigen-presenting cells, in particular by the mature dendritic cells, thereby eliciting an immune response against the cancer cells.

Bacterial Ghosts (BGs) are empty bacterial cell envelopes of bacteria, in particular, of Gram-negative bacteria. Preferred bacteria are *E. coli, Salmonella* or any other Gram-negative bacteria and, in particular, *E. coli* Nissle 1917. The Bacterial Ghosts included in the composition for use according to the invention are derived, in particular, from Gram-negative bacteria, preferably from *E. coli*, more preferably from *E. coli* Nissle 1917.

BGs can be produced by controlled expression of heterologous gene causing disruption of bacterial membrane integrities and leading to lysis of the bacteria. An example of lytic gene is the bacteriophage PhiX174 gene E encoding a polypeptide triggering the fusion of the inner and outer membranes of the bacterial cells and forming trans-membrane tunnel structure spanning the whole cell envelope, through which the entire cytoplasmic content is expelled due to the change in osmotic pressures between the cell interior and the culture medium, whilst the inner and outer membrane structures are preserved and remain intact (cf. U.S. Pat. No. 7,968,323 B2). The size of the trans-membrane tunnel structure depends on the lysis conditions and inner diameter is in the range of 20-400 nm. The empty body of BGs is devoid of nucleic acids, ribosomes and other constituents, whereas essential inner and outer membrane structures including the antigenic molecules, e.g. outer membrane proteins, adhesins, LPS and peptidoglycans are non-denatured and remain intact. There is absolutely no risk of reversal to pathogenic form after induction of controlled lysis process.

Bacterial Ghosts may be prepared by a method comprising the following steps:

(a) providing bacterial cells comprising a gene encoding a lytic protein capable of forming a tunnel structure in the bacterial cell envelope (b) optionally cultivating the bacterial cells under conditions wherein the lytic gene is not expressed (c) subjecting the bacterial cell to conditions wherein the lytic gene is expressed and the cytoplasmic components of the bacterial cells are liberated and (d) obtaining the resulting Bacterial Ghosts.

A preferred example of a gene encoding the lytic protein is the bacteriophage PhiX174 gene E.

The Bacterial Ghosts included in the composition for use according to the invention are preferably obtained from bacterial cells comprising a gene encoding a lytic protein.

Particularly preferred, the bacterial cells used for the above described method of bacterial ghost preparation additionally encode an enzyme capable of hydrolyzing cytoplasmic components in the bacterial cell as described in WO 03/006630. The corresponding method of bacterial ghost preparation comprises the following additional steps:

(a) optionally cultivating the bacterial cells under conditions wherein the enzyme gene is not expressed (b) subjecting the bacterial cell to conditions wherein the enzyme gene is expressed and the cytoplasmic components of the bacterial cells are degraded.

The gene encoding the hydrolytic enzyme is preferably a nuclease gene, in particular a *Staphylococcus aureus* nuclease gene (WO 03/006630).

Although the lysis process is very effective, there still might be a potential contamination with approximately one intact bacterial cell per 10,000 BGs. To avoid the presence of any living cell in a BG preparation, in particular, already before lyophilization of BG samples, an alkylating agent such as beta-propiolactone reacting and causing alterations in nucleic acids is preferably added to the fermentation system prior to final harvesting of BGs. A production process using beta-propiolactone for final inactivation meeting the criteria for application in human medicine and veterinary is disclosed in Patent Application No. PCT/EP2009/000272.

Preferably, the Bacterial Ghosts included in the composition for use according to the invention have been treated with β-propiolactone The use of Bacterial Ghosts as a vaccine or adjuvant and the preparation of recombinant Bacterial Ghosts carrying heterologous proteins in their cell envelope structures are disclosed in Patent Application No. PCT/EP98/04723.

In one embodiment the Bacterial Ghosts are recombinant Bacterial Ghosts, preferably carrying one or more tumor-associated antigens, e.g. tumor-associated antigens previously shown to be expressed by particular tumor cells. The tumor-associated antigens include NY-ESO-1, MAGE-A3, WT1 or RHAMM.

The active agent to be included in the inventive composition can be any suitable active agent, in particular any active agent suitable in the treatment of cancer. Preferably, the active agent is a chemotherapeutic drug. Particular examples of chemotherapeutic drugs include doxorubicin, oxaliplatin, cisplatin, resveratrol, epirubicin, idarubicin, mitoxantrone, cyclophosphamide, maphosphamide, bortezomib or bleomycin.

In a preferred embodiment the chemotherapeutic drug is a chemotherapeutic drug capable of inducing immunogenic cell death.

In the human body millions of cells undergo cell death every second. This physiological programmed cell death (apoptosis) is thought to be incapable of triggering an immune response as apoptotic cells are cleared without inducing local and/or systemic inflammation. In contrast destruction of cells via an infectious or toxic agent is immunogenic, i.e. activates the immune system. Immunogenic cell death does not occur naturally but only under specific stress. In situ administration of BGs loaded with defined chemotherapeutic drugs induces such immunogenic cell death mechanisms. The term "immunogenic cell death" as used herein relates to cancer cell death able to trigger inflammation and activate the immune system against dead cell antigens which are able to elicit strong tumor-antigen specific immune response.

In particular the chemotherapeutic drug capable of inducing immunogenic cell death is oxaliplatin, doxorubicin, epirubicin, idarubicin, mitoxantrone, cyclophosphamide, bortzomib or bleomycin.

In another preferred embodiment the chemotherapeutic drug is a platinum-based chemotherapeutic drug, preferably oxaliplatin or cisplatin, more preferably oxaliplatin.

The term "active agent" as used according to the invention does not include antigen-presenting cells, in particular dendritic cells. In a further preferred embodiment the term "active agent" does not include tumor-associated antigens. Preferably, the term "active agent" according to the present invention does not include antigen-presenting cells and/or tumor-associated antigens.

BGs and active agent can be administered separately. The active agent can be administered at the same time, e.g. on the same day, as the Bacterial Ghosts and/or alternating with administration of the Bacterial Ghosts, e.g. on different days. If the Bacterial Ghosts and the active agent are administered on the same day, it is preferred to administer the Bacterial Ghosts prior to administration of the active agent. It is particularly preferred to administer the Bacterial Ghosts at least 10 min, 20 min, 30 min, 40 min, 50 min, 1 h, preferably 10 min before administration of the active agent. One dose of the active agent is preferably administered on the same day as the Bacterial Ghosts and in addition a further dose of the active agent is administered in between two consecutive administrations of the Bacterial Ghosts.

The active agent can be administered as recommended by the manufacturer. For example, the active agent can be administered in the form of an injectable solution.

Alternatively, the Bacterial Ghosts can be administered together with the active agent, e.g. mixed with the active agent or loaded with the active agent. The use of Bacterial Ghosts as carrier or targeting vehicle of active compounds is disclosed in Patent Application No. PCT/EP00/01906. If the Bacterial Ghosts are loaded with the active agent it is preferred that the active agent is immobilized within the Bacterial Ghosts. Suitable ways to immobilize the active agent within Bacterial Ghosts are described, for example, in Patent Application No. PCT/EP00/01906.

The composition for use according to the invention further comprises a pharmaceutically acceptable carrier and/or excipient. The carrier may be any suitable carrier known in the art such as water, salt solution, e.g. saline, glucose solution for injection. The excipient may be any suitable excipient known in the art such as liposomes, nanoparticles, threhalose, mannitol or dextrans.

The term "pharmaceutically acceptable carrier and/or excipient" as used according to the invention does not include antigen-presenting cells, in particular dendritic cells. In a further preferred embodiment the term "pharmaceutically acceptable carrier and/or excipient" does not include tumor-associated antigens.

The composition for use according to the invention preferably comprises from $10^8$ to $10^{11}$, in particular $10^8$, $10^9$, $10^{10}$, $2\times10^{10}$, most preferable $2\times10^{10}$ Bacterial Ghosts per kg body weight.

The Bacterial Ghosts or the composition comprising Bacterial Ghosts are preferably administered 1 to 10 times, preferably 1 to 5 times and most preferably once or twice or 2 to 10 times, preferably 2 to 5 times, and most preferably twice.

The Bacterial Ghosts or the composition comprising Bacterial Ghosts are preferably administered once or twice to a patient with $2\times10^{10}$ BGs/kg for the first dose and $10^{10}$ BGs/kg for the second and following doses whenever necessary. Thus, in a preferred embodiment, the composition of the invention is for single administration and comprises $2\times10^{10}$ BGs/kg body weight. In a further preferred embodiment, the composition of the invention is for twofold administration and comprises $2\times10^{10}$ BGs/kg body weight for the first dose and $1\times10^{10}$ BGs/kg body weight for the second dose. In a further preferred embodiment, the composition of the invention is for multiple administration and comprises $2\times10^{10}$ BGs/kg body weight for the first dose and $1\times10^{10}$ BGs/kg body weight for any further dose.

The composition for use according to the invention can be administered in any suitable way. It is preferred to administer the composition topically, intradermally, subcutaneously, orally, rectally, vaginally, intraperitoneally, intratumorally, peritumorally, and/or by intravesical instillation, preferably peritumorally or intratumorally The composition for use according to the invention is particularly useful in the treatment of cancer selected from selected from bladder carcinoma, breast carcinoma, colon carcinoma, colorectal carcinoma, Head and Neck Squamous Cell Carcinoma (HNSCC), liver carcinoma, lung carcinoma lymphoma, melanoma, mesothelioma, monocytic and myeloid leukemia, myeloma, ovarian carcinoma, pancreas carcinoma, peritoneal carcinomatosis, renal carcinoma and/or non-melanoma skin cancer. Preferably the cancer is ovarian carcinoma, bladder carcinoma or peritoneal carcinomatosis. In a further preferred embodiment the cancer is colorectal carcinoma.

The composition for use according to the invention significantly reduces or terminates tumor progression, preferably the composition for use significantly reduces or eliminates tumor burden, most preferably the composition for use leads to tumor remission. The effects of the composition for use according to the invention result in extended period of stable disease, temporary or permanent disease-free status and overall in an improved quality of life.

The composition for use according to the invention is particularly useful for the treatment of residual primary tumor and/or tumor metastasis.

In a further embodiment the present invention provides a composition comprising Bacterial Ghosts, optionally an active agent, and a pharmaceutically acceptable carrier and/or excipient for use in the prevention of cancer. Therefore, the composition for use as described hereinabove is administered to a subject predisposed for the development of cancer, in particular intradermally. In this embodiment the Bacterial Ghosts are either plain Bacterial Ghosts or Bacterial Ghosts carrying defined tumor-associated antigens.

In a preferred embodiment, the invention relates to a composition for use as described hereinabove, wherein the composition comprises Bacterial Ghosts, and a pharmaceutically acceptable carrier and/or excipient and wherein the composition does not comprise tumor-associated antigens and/or antigen-presenting cells, in particular dendritic cells.

In a further preferred embodiment, the invention relates to a composition for use as described hereinabove, wherein the composition comprises Bacterial Ghosts, an active agent, and a pharmaceutically acceptable carrier and/or excipient and wherein the composition does not comprise tumor-associated antigens and/or antigen-presenting cells, in particular dendritic cells.

In another preferred embodiment the invention relates to a composition for use as described hereinabove, wherein the composition is consisting of (i) Bacterial Ghosts, (ii) optionally an active agent, and (iii) a pharmaceutically acceptable carrier and/or excipient.

In a particularly preferred embodiment the invention relates to a composition for use as described hereinabove, wherein the composition is consisting of (i) Bacterial Ghosts, and (ii) a pharmaceutically acceptable carrier and/or excipient.

In a further particularly preferred embodiment the invention relates to a composition for use as described hereinabove, wherein the composition is consisting of (i) Bacterial Ghosts, (ii) an active agent, and (iii) a pharmaceutically acceptable carrier and/or excipient.

The composition as described hereinabove is particularly useful as a vaccine for tumor immunotherapy.

According to the invention it has particularly been found that the administration of Bacterial Ghosts leads to a reduction of PD1 expression on $CD8^+$ cytotoxic T cells and of PD-L1 on tumor cells.

Therefore, the invention provides compositions and methods for (re)stimulation of the immune system of a patient by interfering with PD1-/PD-L1-mediated signaling and function. According to the invention, interfering with PD1-/PD-L1-mediated signaling and function is to be understood as downregulating and/or inhibiting PD1-/PD-L1-mediated signaling and function. Downregulation and/or inhibition of PD1-/PD-L1-mediated signaling and function is achieved by a reduction of PD1 receptor and/or by a reduction of PD-L1 on cells in the TME. Preferably, downregulation and/or inhibition of PD1-/PD-L1-mediated signaling and function is achieved by a reduction of PD1 receptor on immune cells in the TME in particular on CD8+ cytotoxic T cells in the TME, and/or by a reduction of PD-L1 on tumor cells in the TME.

Accordingly, the Bacterial Ghosts or the composition comprising Bacterial Ghosts as described hereinabove is useful to obtain a reduction of PD-L1-positive cells in the TME, in particular to obtain a reduction of PD-L1-positive cancer cells in the TME. Further, the Bacterial Ghosts or the composition comprising Bacterial Ghosts as described hereinabove is useful to obtain a reduction of PD1-positive cells in the TME, in particular to obtain a reduction of PD1-positive CD8+ cytotoxic T cells in the TME.

In particular, the invention relates to Bacterial Ghosts or the composition comprising Bacterial Ghosts as described hereinabove for use for the inhibition of PD1-/PD-L1-mediated cellular signaling and suppressive activities in immune cells and/or cancer cells.

In particular, the invention relates to Bacterial Ghosts or the composition comprising Bacterial Ghosts for use in the treatment or prevention of cancer or other pathological disorders modulated by PD1-/PD-L1-mediated functions.

The invention further provides a method of using Bacterial Ghosts or the composition comprising Bacterial Ghosts for the inhibition of PD1-/PD-L1-mediated cellular signaling and suppressive activities in immune cells and/or cancer cells comprising the step of administering Bacterial Ghosts to a person determined to have cancer or to be otherwise in need of PD1-/PD-L1 antagonism.

In order to further enhance effectiveness of the Bacterial Ghosts or the composition comprising Bacterial Ghosts with respect to the inhibition of PD1-/PD-L1-mediated cellular signaling and suppressive activities in immune cells and/or cancer cells, antibodies against PD1 receptor and/or PD-L1 can be included as the active agent in the composition, optionally in addition to a chemotherapeutic agent.

The invention is further described by the enclosed Figures and the following Examples.

FIGURES

FIG. 1. Study scheme and treatment schedule of Example 1.

FIG. 2. PD1 and PD-L1 expressions by all cells isolated from harvested tumors after treatment of CT26 tumor bearing mice with *E. coli* Nissle 1917 BGs.

FIG. 3. Treatment of CT26 tumor bearing mice with *E. coli* Nissle 1917 BGs modifies the number of lymphocytes present within the tumor microenvironment.

FIG. 4. Treatment of CT26 tumor bearing mice with *E. coli* Nissle 1917 BGs alters the number of antigen-presenting cells present within the tumor microenvironment.

FIG. 5. Treatment of CT26 tumor bearing mice with *E. coli* Nissle 1917 BGs doesn't modulate populations of PD1 expressing cancer cells obtained from tumor, but has impact on tumor infiltration by T cells.

FIG. 6. Treatment of CT26 tumor bearing animals with *E. coli* Nissle 1917 BGs reduces the number of PD-L1 positive cells within the tumor microenvironment.

FIG. 7. Treatment of CT26 tumor bearing animals with *E. coli* Nissle 1917 BGs modulate populations of PD-L1 positive antigen-presenting cells present within the tumor microenvironment.

FIG. 8. Study scheme and treatment schedule of Example 2.

FIG. 9. Tumor burden assessment after the treatment of CT26 tumor bearing mice with either oxaliplatin alone or combined with *E. coli* Nissle 1917 BGs.

EXAMPLES

Example 1

Effect of *E. coli* Nissle 1917 BGs on Cells of Tumor Microenvironment after Treatment of CT26 Bearing Mice Summary The aim of the study was to assess the impact of Bacterial Ghosts (BGs) on the expression of programmed cell death protein 1 (PD1) and its ligand (PD-L1), known to be actively involved in the immune checkpoint pathway, by cells present within the tumor microenvironment, and on the presence of immune cells infiltrating the tumor. Expression levels of PD1 and PD-L1 were analyzed on cells isolated from harvested tumors of intraperitoneally inoculated CT26 colorectal carcinoma bearing mice treated with single (Group #2) or double doses (Group #3) of BGs generated from probiotic Gram-negative strain *E. coli* Nissle 1917 administered intraperitoneally at the same place as used for tumor inoculation. Mice who received no treatment served as control (Group #1).

Multicolor flow cytometry analysis of all tumor cells (population of all cells isolated from harvested tumors of each animal as single cell suspension including cancer cells, non-immune and immune cells) showed no change in expression levels of co-inhibitory receptor PD1. However, detailed investigation revealed increased numbers of PD1 positive CD45+CD3+CD4+ expressing helper T cells. In contrast to that we detected reduced numbers of PD1 positive CD45+CD3+CD8+ expressing cytotoxic T cells. Moreover, we detected very moderate effect of *E. coli* Nissle 1917 BGs on the PD1 expression by cancer cells defined as CD45-negative (CD45−) population of all cells isolated from harvested tumors.

Treatment of tumor bearing animals with *E. coli* Nissle 1917 BGs markedly reduced percentage of cancer cells (CD45− cells) expressing PD-L1 within the tumor microenvironment. Single treatment of tumor bearing animals by *E. coli* Nissle 1917 BGs also negatively affected percentage of PD-L1 expressing CD45-positive (CD45+) lymphocytes, but this effect was not as significant as observed for CD45− cancer cells. Moreover, treatment with two doses of *E. coli* Nissle 1917 BGs had even lower effect on number of PD-L1 expressing CD45+ lymphocytes. Similar effect was detected for tumor infiltrating macrophages defined as CD45+F4/80+ cells, where single treatment of tumor bearing mice by *E. coli* Nissle 1917 BGs partially decreased the number of PD-L1 positive cells, but two doses treatment had reduced efficacy compared to single BGs treatment. Furthermore, there was no difference detected between PD-L1 expressing M2 tumor infiltrating macrophages defined as CD45+F4/80+CD206+ cells isolated from tumors of animals without the treatment and animals who received single treatment with *E. coli* Nissle 1917 BGs. However, two doses treatment with *E. coli* Nissle 1917 BGs slightly decreased number of PD-L1 positive M2 macrophages present within the tumors. Besides, there was no difference detected in expression levels of PD-L1 by tumor infiltrating dendritic cells defined as CD45+CD11c+ cells in all examined groups.

Detailed analysis confirmed increased numbers of tumor infiltrating CD45+CD3+CD4+ helper T cells and CD45+CD11c+ dendritic cells which positively correlated with increased treatment doses. Treatment of tumor bearing mice with *E. coli* Nissle 1917 BGs also very slightly enhanced number of tumor infiltrating CD45$^+$CD3$^+$CD8$^+$ cytotoxic T cells. In contrast, *E. coli* Nissle 1917 BGs treatment led to reduced numbers of tumor infiltrating M2 CD45$^+$F4/80$^+$CD206$^+$ macrophages and more significantly of CD45$^+$F4/80$^+$ macrophages.

Above all results obtained from multicolor flow cytometry, examinations of animals at the section day showed no tumor presence in two out of eight animals who received single treatment with *E. coli* Nissle 1917 BGs (Group #2) and no tumor presence in four out of nine animals who received two doses treatment with *E. coli* Nissle 1917 BGs (Group #3) and one animal which died before day 14 after treatment (double BG treatment—1/9; day 13 after treatment start).

All animals from control group (Group #1) without the treatment had at the section day fully developed tumors.

Results

FIG. 1

The mice were inoculated intraperitoneally (lower left quadrant) with 1×10$^5$ cells of CT26 mouse colorectal carcinoma cells and randomly distributed into the three groups (D1). Three days after tumor inoculation (D4) the first group of animals (Group #1) received 100 μl of 5% glucose solution for injection administered intraperitoneally at the same place as used for tumor inoculation. Mice from Group #2 and Group #3 were injected intraperitoneally at the D4 with 4×10$^8$ *E. coli* Nissle 1917 BGs reconstituted in 100 μl of 5% glucose solution for injection at the same place as used for tumor inoculation. Seven days after the first round of treatment (D11), mice from the Group #3 received the second dose of *E. coli* Nissle 1917 BGs (1×10$^8$) reconstituted in 100 μl of 5% glucose solution for injection and administered intraperitoneally at the same place as tumor inoculation and the first treatment administration. Mice from Group #1 and Group #2 received no additional treatment. All mice were sacrificed 14 days (D18) after the treatment initiation (D4). One animal from Group #3 (double BG treatment—1/9) died before day 14 after treatment (day 13 after treatment start).

FIG. 2

PD1 (A) and PD-L1 (B) expressions were assessed on population of all cells obtained from harvested tumors of each animal as single cell suspension (all tumor cells) 14 days after treatment initiation. Number of tumors examined differs due to cases where no tumor presence was detected (single BG treatment—2/8; double BG treatment—4/9) and where animal died before day 14 after treatment (double BG treatment—1/9; day 13 after treatment start). Treatment of CT26 tumor bearing animals with both single (4×10$^8$ at day D4) and two doses (4×10$^8$ at day D4 and 1×10$^8$ at day D11) of *E. coli* Nissle 1917 BGs did not alter the percentage of PD1 expressing cells within the tumor microenvironment. However, reduced numbers of PD-L1 expressing cells were detected after treatment of mice with both single and double doses of *E. coli* Nissle 1917 BGs.

FIG. 3

Treatment of tumor bearing animals with both single (4×10$^8$ at day D4) and double doses (4×10$^8$ at day D4 and 1×10$^8$ at day D11) of *E. coli* Nissle 1917 BGs decreased the number of total CD45-positive cells (A). In contrast, we detected increased presence of CD45$^+$CD3$^+$ T cells after both treatments with *E. coli* Nissle 1917 BGs (B) with more potent tumor infiltration by CD45$^+$CD3$^+$CD4$^+$ helper T cells (C). In addition to that, a small increase of CD45$^+$CD3$^+$CD8$^+$ cytotoxic T cells presence was detected after treatment with *E. coli* Nissle 1917 BGs (D). Number of tumors examined differs due to cases where no tumor presence was detected (single BG treatment—2/8; double BG treatment—4/9) and where animal died before day 14 after treatment (double BG treatment—1/9 day 13 after treatment start).

FIG. 4

Treatment of tumor bearing animals with both single (4×10$^8$ at day D4) and double doses (4×10$^8$ at day D4 and 1×10$^8$ at day D11) of *E. coli* Nissle 1917 BGs enhanced the number of CD45$^+$CD11c$^+$ dendritic cells infiltrating the tumor (A). Decreased number of CD45$^+$F4/80$^+$ macrophages was detected in the tumors after both single and double treatments with *E. coli* Nissle 1917 BGs (B). Similar, but lower trend was detected for CD45$^+$F4/80$^+$CD206$^+$ (M2) macrophages present within the tumor microenvironment (C). Number of examined tumors differs due to cases where no tumor presence was detected (single BG treatment—2/8; double BG treatment—4/9) and where animal died before day 14 after treatment (double BG treatment—1/9; day 13 after treatment start).

FIG. 5

No substantial changes in total numbers of PD1 expressing tumor cells (A), CD45$^-$ cancer cells (B) and CD45$^+$ lymphocytes (C) were detected after treatment of tumor bearing animals with *E. coli* Nissle 1917 BGs. However, detailed assessment of PD1 positive T cells within the tumor microenvironment revealed changes in numbers of CD45$^+$CD3$^+$ T cells (D), where both treatment regimens with *E. coli* Nissle 1917 increased numbers of PD1 positive CD45$^+$CD3$^+$CD4$^+$ helper T cells (E), but reduced numbers of PD1 positive CD45$^+$CD3$^+$CD8$^+$ expressing cytotoxic T cells (F). Number of examined tumors differs due to cases where no tumor presence was detected (single BG treatment—2/8; double BG treatment—4/9) and where animal died before day 14 after treatment (double BG treatment—1/9; day 13 after treatment start).

FIG. 6

Treatment of mice with both single (4×10$^8$ at day D4) and double doses (4×10$^8$ at day D4 and 1×10$^8$ at day D11) of *E. coli* Nissle 1917 BGs reduced numbers of PD-L1 positive cells in tumors (A) and had more noticeable impact on cancer cells (B) than on CD45$^+$ lymphocytes where decreased numbers PD-L1 positive cells were detected only in tumors obtained from animals who received single treatment with *E. coli* Nissle 1917 BGs (C). Number of examined tumors differs due to cases where no tumor presence was detected (single BG treatment—2/8; double BG treatment—4/9) and where animal died before day 14 after treatment (double BG treatment—1/9; day 13 after treatment start).

FIG. 7

Treatment of mice with both single (4×10$^8$ at day D4) and double doses (4×10$^8$ at day D4 and 1×10$^8$ at day D11) of *E. coli* Nissle 1917 BGs did not change number of PD-L1 positive CD45$^+$CD11c$^+$ dendritic cells (A). A single treatment with *E. coli* Nissle 1917 BGs reduced number of CD45$^+$F4/80$^+$ PD-L1 positive macrophages, but no effect was detected after administration of two *E. coli* Nissle 1917 BG's doses (B). The opposite effect was detected for PD-L1 expressing CD45$^+$F4/80$^+$CD206$^+$ (M2) macrophages where single treatment with *E. coli* Nissle 1917 BGs didn't change number of PD-L1 positive cells, but two doses treatment reduced number of CD45$^+$F4/80$^+$CD206$^+$ PD-L1$^+$ (M2) macrophages (C). Number of examined tumors differs due to cases where no tumor presence was detected (single BG treatment—2/8; double BG treatment—4/9) and where animal died before day 14 after treatment (double BG treatment—1/9; day 13 after treatment start).

Example 2

Effect of *E. coli* Nissle 1917 BGs and Oxaliplatin Combination on Tumor Burden after Treatment of CT26 Bearing Mice Summary The aim of the study was to assess the impact of Bacterial Ghosts' (BGs) mediated effect on the tumor progression in vivo with the parallel treatment with chemotherapeutic drug.

Mice intraperitoneally inoculated with CT26 colorectal carcinoma cells were treated either with oxaliplatin alone or combined with BGs generated from *E. coli* Nissle 1917, and observed for fourteen days after therapy initiation. Treatment of mice started three days after tumor inoculation and comprised of either one or two cycles of BGs administration combined with either two or four drug administrations, respectively. Furthermore, part of mice was treated with either two or four drug administrations without the extra addition of BGs. Survival and animal behavior were monitored until the section day; animal weights were documented once per week. Tumor presence and burden were assessed at the section day including organ screening and photo documentation.

Obtained results clearly indicate the efficacy of two cycles regimen comprising combination of *E. coli* Nissle 1917 BGs and oxaliplatin by showing a greater reduction of tumor burden as compared to tumor mass reduction detected after single cycle treatment either with drug alone or after combination of drug with BGs.

Moreover, two cycles combination treatment regimen comprising BGs and drug was even more efficient than two cycles treatment regimen with drug alone. Besides that, first administration of BGs during the treatment utilizing two cycles combination regimen showed even greater reduction of tumor burden than the treatment with the same regimen but with administration of drug first.

Altogether obtained results clearly indicate BGs' mediated beneficial effect on tumor burden reduction during the treatment of mice bearing intraperitoneally inoculated tumor with two cycles regimen combining the use of chemotherapeutic drug and BGs.

Results

FIG. 8

The mice were inoculated intraperitoneally (in lower left quadrant) with $1 \times 10^5$ cells of CT26 mouse colorectal carcinoma cells and randomly distributed into the seven groups (D1).

Three days after tumor inoculation (D4) the first group of animals (Group #1) received 100 µl of 5% glucose solution for injection (solvent) administered intraperitoneally at the same place as used for tumor inoculation.

Mice from Group #2.1 were injected intraperitoneally at D4 and D6 (five days after tumor inoculation) with 6 mg/kg oxaliplatin reconstituted in 100 µl of 5% glucose solution for injection at the same place as used for tumor inoculation.

Mice from Group #2.2 were injected intraperitoneally at D4, D6, D11 (ten days after tumor inoculation) and D13 (twelve days after tumor inoculation) with 6 mg/kg oxaliplatin reconstituted in 100 µl of 5% glucose solution for injection at the same place as used for tumor inoculation.

Mice from Group #3.1 and Group #4.1 were injected intraperitoneally at D4 with $4 \times 10^8$ *E. coli* Nissle 1917 BGs reconstituted in 100 µl of 5% glucose solution for injection at the same place as used for tumor inoculation. In addition mice from Group #3.1 and Group #4.1 were injected intraperitoneally at D4, and D6 with 6 mg/kg oxaliplatin reconstituted in 100 µl of 5% glucose solution for injection at the same place as used for tumor inoculation.

Mice from Group #3.2 and Group #4.2 were injected intraperitoneally at D4 with $4 \times 10^8$ *E. coli* Nissle 1917 BGs reconstituted in 100 µl of 5% glucose solution for injection at the same place as used for tumor inoculation. In addition mice from Group #3.2 and Group #4.2 were injected intraperitoneally at D4 and D6 with 6 mg/kg oxaliplatin reconstituted in 100 µl of 5% glucose solution for injection at the same place as used for tumor inoculation. Seven days after the first round of treatment (D11), mice from Group #3.2 and Group #4.2 received the second dose of *E. coli* Nissle 1917 BGs ($1 \times 10^8$) reconstituted in 100 µl of 5% glucose solution for injection and administered intraperitoneally at the same place as tumor inoculation and the first treatment administration. In addition mice from Group #3.2 and Group #4.2 were injected intraperitoneally at D11 and D13 with 6 mg/kg oxaliplatin reconstituted in 100 µl of 5% glucose solution for injection at the same place as used for tumor inoculation.

Mice from Group #3.1 and Group #3.2 received first treatment with oxaliplatin followed by administration of *E. coli* Nissle 1917 BGs. Mice from Group #4.1 and Group #4.2 received first treatment with *E. coli* Nissle 1917 BGs followed by administration of oxaliplatin. Both treatments were administered within 10 minutes period of time.

All mice were sacrificed 14 days (D18) after the treatment initiation (D4).

FIG. 9

CT26 intraperitoneal carcinoma bearing mice were treated either with one (A) or two (B) cycles of therapy. One cycle treatment comprises intraperitoneal administration of $4 \times 10^8$ *E. coli* Nissle 1917 BGs three days after tumor inoculation (D4) and intraperitoneal administrations of 6 mg/kg oxaliplatin three (D4) and five (D6) days after tumor inoculation. Two cycles treatment comprises intraperitoneal administrations of $4 \times 10^8$ *E. coli* Nissle 1917 BGs at D4 and $1 \times 10^8$ *E. coli* Nissle 1917 BGs at day ten (D11) after tumor inoculation, and along with intraperitoneal administrations of 6 mg/kg oxaliplatin at D4, D6, D11 and D13 (day twelve after tumor inoculation). Control group of animals received 100 µl of 5% glucose solution for injection (solvent) administered intraperitoneally at the same place as used for tumor inoculation. Two groups of mice (one and two cycles treatment) received first treatment with oxaliplatin followed by administration of *E. coli* Nissle 1917 BGs (oxaliplatin+BGs). Two groups of mice (one and two cycles treatment) received first treatment with *E. coli* Nissle 1917 BGs followed by administration of oxaliplatin (BGs+oxaliplatin). Both BGs and drug were administered within 10 minutes period of time. Tumors of each animal were harvested fourteen days after treatment initiation (D18). Collected tumor tissues were weighted to determine the tumor burden reduction in comparison to control as the treatment efficacy. Results clearly indicate that the use of two cycles treatment regimen comprising combination of *E. coli* Nissle 1917 BGs and oxaliplatin leads to reduced tumor burden as compared to single cycle treatment either with drug alone or combined with BGs. Furthermore, two cycles treatment regimen comprising combination of *E. coli* Nissle 1917 BGs and oxaliplatin was more efficient that two cycles treatment regimen with drug alone. Moreover, mice treated first with BGs (BGs+oxaliplatin) had even more reduced tumor burden than those treated the same combination but with administration of drug first (oxaliplatin+BGs).

The invention claimed is:

1. A method of stimulating an anti-tumor immune response in a patient, comprising administering to the patient a composition comprising
   (i) Bacterial Ghosts obtained from *Escherichia coli* Nissle 1917 and
   (ii) a pharmaceutically acceptable carrier and/or excipient.

2. The method of claim 1, wherein the composition further comprises
   (iii) an active agent, wherein the active agent is a chemotherapeutic drug.

3. The method of claim 2, wherein the active agent is a platinum-based chemotherapeutic drug.

4. The method of claim 2, wherein the Bacterial Ghosts are mixed or loaded with the active agent.

5. The method of claim 1, wherein the composition is administered topically, intradermally, subcutaneously, orally, rectally, vaginally, intraperitoneally, intratumorally, peritumorally, by intravesical instillation, or by a combination of two or more thereof.

6. The method of claim 1, wherein the Bacterial Ghosts are recombinant Bacterial Ghosts carrying one or more tumor-associated antigens.

7. The method of claim 1, wherein the anti-tumor immune response is an immune response against a residual primary tumor and/or tumor metastasis.

8. The method of claim 1, wherein the Bacterial Ghosts are obtained from bacterial cells comprising a gene encoding a lytic protein.

9. The method of claim 1, wherein the Bacterial Ghosts have been treated with β-propiolactone.

10. The method of claim 1, wherein the composition is administered at a dose comprising $2 \times 10^{10}$ Bacterial Ghosts per kg body weight for first dose and $10^{10}$ BGs/kg for second and following doses.

11. The method of claim 1, wherein the anti-tumor immune response is an immune response against at least one of bladder carcinoma, breast carcinoma, colon carcinoma, colorectal carcinoma, Head and Neck Squamous Cell Carcinoma (HNSCC), liver carcinoma, lung carcinoma, lymphoma, melanoma, mesothelioma, monocytic and myeloid leukemia, myeloma, ovarian carcinoma, pancreas carcinoma, peritoneal carcinomatosis, renal carcinoma or non-melanoma skin carcinoma.

12. The method of claim 1, wherein the composition consists of
   (i) the Bacterial Ghosts, and
   (ii) the pharmaceutically acceptable carrier and/or excipient.

13. The method of claim 2, wherein the chemotherapeutic drug comprises at least one of doxorubicin, oxaliplatin, resveratrol, epirubicin, idarubicin, mitoxantrone, cyclophosphamide, maphosphamide, bortezomib or bleomycin.

14. The method of claim 3, wherein the platinum-based chemotherapeutic drug comprises oxaliplatin.

15. The method of claim 4, wherein the active agent is immobilized within the bacterial ghosts.

16. The method of claim 1, wherein the patient is a cancer patient.

17. The method of claim 1, wherein the patient is a patient predisposed to cancer.

18. The method of claim 2, wherein the composition consists of
   (i) the Bacterial ghosts,
   (i) the pharmaceutically acceptable carrier and/or excipient, and
   (iii) the active agent.

* * * * *